US010232350B2

(12) United States Patent
Lee et al.

(10) Patent No.: US 10,232,350 B2
(45) Date of Patent: Mar. 19, 2019

(54) PHOTOCATALYST FUNCTIONAL FILM AND METHOD FOR PRODUCING THE SAME

(71) Applicant: LG HAUSYS, LTD., Seoul (KR)

(72) Inventors: Dong-Il Lee, Anyang-si (KR); Joo-Hwan Seo, Seoul (KR); Hyun-Jae Kim, Seoul (KR); Hye-Youn Jang, Ansan-si (KR); Seong-Moon Jung, Daejeon (KR)

(73) Assignee: LG HAUSYS, LTD., Seoul (KR)

( * ) Notice: Subject to any disclaimer, the term of this patent is extended or adjusted under 35 U.S.C. 154(b) by 0 days.

(21) Appl. No.: 15/329,898

(22) PCT Filed: Jul. 31, 2015

(86) PCT No.: PCT/KR2015/008067
§ 371 (c)(1),
(2) Date: Jan. 27, 2017

(87) PCT Pub. No.: WO2016/021889
PCT Pub. Date: Feb. 11, 2016

(65) Prior Publication Data
US 2017/0259246 A1 Sep. 14, 2017

(30) Foreign Application Priority Data
Aug. 6, 2014 (KR) ........................ 10-2014-0101039

(51) Int. Cl.
*A61L 9/18* (2006.01)
*C08J 5/18* (2006.01)
(Continued)

(52) U.S. Cl.
CPC ................ *B01J 23/30* (2013.01); *A61L 9/18* (2013.01); *B01J 21/063* (2013.01); *B01J 21/08* (2013.01);
(Continued)

(58) Field of Classification Search
CPC . B01J 23/30; B01J 21/063; B01J 21/08; B01J 23/42; B01J 35/004; B01J 35/023;
(Continued)

(56) References Cited

U.S. PATENT DOCUMENTS 4,277,525 A * 7/1981 Nakayama ........... C09D 183/02
106/218
6,107,241 A * 8/2000 Ogata .................... B01J 21/063
423/608
(Continued)

FOREIGN PATENT DOCUMENTS

CN 1401085 A 3/2003
CN 1974890 A 6/2007
(Continued)

OTHER PUBLICATIONS

International Search Report dated Oct. 28, 2015 corresponding to International Application PCT/KR2015/008067.
(Continued)

*Primary Examiner* — Melvin C. Mayes
*Assistant Examiner* — Michael Forrest
(74) *Attorney, Agent, or Firm* — Hauptman Ham, LLP

(57) ABSTRACT

A photocatalytic functional film has a structure of a substrate, a barrier layer and a photocatalytic layer stacked one on another. The barrier layer is a $SiO_2$ film, the photocatalyst layer comprises an amorphous $TiO_2$ film, and particles of visible light responsive photocatalytic material formed on the surface of the amorphous $TiO_2$ film. A method for producing a photocatalytic functional film includes: adding an alcohol solvent and an acid to a silicate precursor to obtain a $SiO_2$ sol by dehydration and de-alcoholization reaction; applying and drying the $SiO_2$ sol on a substrate to form a barrier layer; adding an alcohol solvent and an acid to a titanium precursor to obtain a $TiO_2$ amorphous sol by dehydration and de-alcoholization reaction; and applying and drying a composition formed by mixing particles of visible light responsive photocatalyst material with the $TiO_2$ amorphous sol on the barrier layer, to form a photocatalyst layer.

12 Claims, 1 Drawing Sheet

(51) Int. Cl.
*G02B 1/10* (2015.01)
*B01J 21/06* (2006.01)
*B01J 21/08* (2006.01)
*B01J 23/30* (2006.01)
*B01J 23/42* (2006.01)
*B01J 35/00* (2006.01)
*B01J 35/02* (2006.01)
*B01J 35/10* (2006.01)
*B01J 37/02* (2006.01)
*C03C 17/34* (2006.01)

(52) U.S. Cl.
CPC .............. *B01J 23/42* (2013.01); *B01J 35/004* (2013.01); *B01J 35/023* (2013.01); *B01J 35/1009* (2013.01); *B01J 35/1014* (2013.01); *B01J 35/1019* (2013.01); *B01J 37/0236* (2013.01); *B01J 37/0244* (2013.01); *C03C 17/3417* (2013.01); *C08J 5/18* (2013.01); *G02B 1/10* (2013.01); *C03C 2217/71* (2013.01)

(58) Field of Classification Search
CPC ................ B01J 35/1009; B01J 35/1014; B01J 35/1019; B01J 37/0236; B01J 37/0244; A61L 9/18; C03C 17/3417; C08J 5/18; G02B 1/10
See application file for complete search history.

(56) References Cited

U.S. PATENT DOCUMENTS

| | | | |
|---|---|---|---|
| 2003/0143437 A1* | 7/2003 | Ohtsu ..................... | A01N 59/16 428/701 |
| 2003/0186089 A1 | 10/2003 | Kikuchi et al. | |
| 2003/0215647 A1 | 11/2003 | Yoshida et al. | |
| 2005/0175852 A1 | 8/2005 | Okudera et al. | |
| 2009/0026063 A1* | 1/2009 | Skiles ................. | B01D 53/864 204/157.3 |
| 2011/0082026 A1* | 4/2011 | Sakatani ................ | B01J 21/063 502/159 |
| 2011/0135861 A1 | 6/2011 | Manzara et al. | |

FOREIGN PATENT DOCUMENTS

| | | |
|---|---|---|
| CN | 101274276 | 10/2008 |
| CN | 102471088 A | 5/2012 |
| EP | 1348675 A1 | 10/2003 |
| EP | 1350772 A1 | 10/2003 |
| GB | 2327428 A | 1/1999 |
| JP | H08-117606 A | 5/1996 |
| JP | H08126845 A | 5/1996 |
| JP | H09313948 A | 12/1997 |
| JP | H10-278168 A | 10/1998 |
| JP | 2002060221 A | 2/2002 |
| JP | 2003-181299 A | 7/2003 |
| JP | 2003-277041 A | 10/2003 |
| JP | 2003-277056 A | 10/2003 |
| JP | 2004-001400 A | 1/2004 |
| JP | 3592727 B2 | 11/2004 |
| JP | 2006289315 A | 10/2006 |
| JP | 4250332 B2 | 1/2009 |
| JP | 2010188226 A | 9/2010 |
| JP | 2011031139 A | 2/2011 |
| KR | 2000-0065270 A | 11/2000 |
| KR | 10-0516203 B1 | 9/2005 |
| KR | 10-2012-0057572 A | 6/2012 |
| KR | 10-2013-0124601 A | 11/2013 |
| WO | 9629375 A1 | 9/1996 |
| WO | 2005110938 A1 | 11/2005 |

OTHER PUBLICATIONS

Extended European Search Report dated Jun. 26, 2017 from European Patent Office in connection with the counterpart European Patent Application No. 15829135.1.
Japanese Notice of Allowance dated May 8, 2018, issued in corresponding Japanese Patent Application No. 2017-506649.
Chinese Office Action dated Mar. 23, 2018, issued in corresponding Chinese Patent Application No. 201580042094.1.
Japanese Office Action dated Jan. 9, 2018, in connection with the counterpart Japanese Patent Application No. 2017-506649.
European Office Action dated Mar. 14, 2018, in connection with the counterpart European Patent Application No. 15829135.1.
The Chinese Office Action dated Nov. 30, 2018 in connection with the counterpart Chinese Patent Application No. 201580042094.1.

* cited by examiner

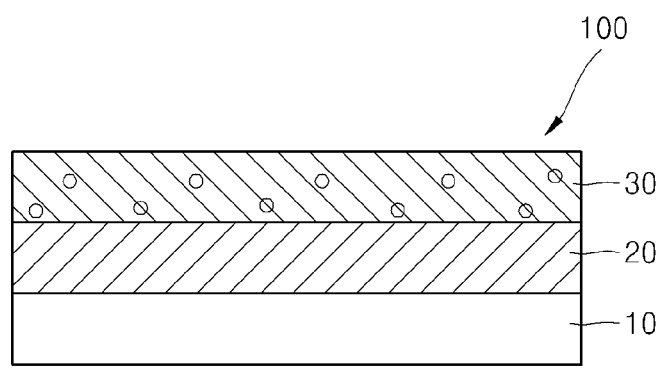

PHOTOCATALYST FUNCTIONAL FILM AND METHOD FOR PRODUCING THE SAME

CROSS-REFERENCE TO RELATED APPLICATIONS

This application claims the priority of Korean Patent Application No. 10-2014-0101039 filed on Aug. 6, 2014, in the Korean Intellectual Property Office. Further, this application is the National Phase Application of International Application No. PCT/KR2015/008067, filed Jul. 31, 2015, which designates the United States and was published in Korean. Both of the priority documents are hereby incorporated by reference in their entireties.

BACKGROUND

1. Technical Field

The present disclosure relates to a photocatalyst functional film and a method for producing the same.

2. Description of the Related Art

A photocatalyst may be coated on the surface of an indoor interior material to improve Indoor Air Quality (IAQ). To coat such photocatalyst, it is essential to use a binder to attach the photocatalyst to a substrate. However, the binder covers the surface of the photocatalyst in the process of coupling with the photocatalyst, thereby reducing the exposed area of the surface of the photocatalyst. As a result, there is a problem in that the binder lowers the performance of the photocatalyst which is in proportion to the surface reaction.

SUMMARY

It is an object of the present disclosure to provide a photocatalytic functional film that uses a binder which does not lowering the efficiency of a photocatalyst and comprises a barrier layer.

It is another aspect of the present disclosure to provide a method for producing the photocatalytic functional film.

In accordance with one aspect of the present disclosure, a photocatalytic functional film has a structure of a substrate, a barrier layer and a photocatalytic layer stacked one on another. The barrier layer is a $SiO_2$ film, the photocatalyst layer comprises an amorphous $TiO_2$ film, and particles of visible light responsive photocatalytic material formed on the surface of the amorphous $TiO_2$ film.

The porosity of the amorphous $TiO_2$ film may range from approximately 5% to 50%.

The specific surface area of the amorphous $TiO_2$ film may range from approximately 5 $m^2/g$ to 500 $m^2/g$.

The amorphous $TiO_2$ film may be formed by a $TiO_2$ amorphous sol.

The particles of the visible light responsive photocatalyst material may be porous metal oxide particles carrying a visible light activating metal containing pores.

The porous metal oxide particles may include at least one selected from a group consisting of titanium oxide, tungsten oxide, zinc oxide, niobium oxide, and a combination thereof.

The porous metal oxide particles may carry the visible light activating metal as a visible light-activating metal or an oxide thereof, and the visible light activating metal may include at least one of tungsten, chromium, vanadium, molybdenum, copper, iron, cobalt, manganese, nickel, platinum, gold, cerium, cadmium, zinc, magnesium, calcium, strontium, barium, or a combination thereof.

The weight ratio of the porous metal oxide and a sum of the visible light activating metal and the visible light activating metal oxide in the particles of the visible light responsive photocatalyst material may range from 99.9:0.1 to 99:1.

The thickness of the barrier layer may range from approximately 20 nm to 500 nm.

The thickness of the photocatalytic layer may range from approximately 50 nm to 500 nm.

The substrate may be an indoor interior material.

In accordance with another aspect of the present disclosure, a method for producing a photocatalytic functional film includes: adding an alcohol solvent and an acid to a silicate precursor to obtain a $SiO_2$ sol by dehydration and de-alcoholization reaction; applying and drying the $SiO_2$ sol on a substrate to form a barrier layer; adding an alcohol solvent and an acid to a titanium precursor to obtain a $TiO_2$ amorphous sol by dehydration and de-alcoholization reaction; and applying and drying a composition formed by mixing particles of visible light responsive photocatalyst material with the $TiO_2$ amorphous sol on the barrier layer, to form a photocatalyst layer.

The alcohol solvent may be at least one selected from the group consisting of isopropyl alcohol, ethanol, methanol, butanol, and combinations thereof.

The composition may contain approximately 20 parts by weight of the $TiO_2$ amorphous sol relative to 100 parts by weight of the particles of the visible light responsive photocatalyst material.

The photocatalytic functional film can achieve indoor air purification, deodorization, antibacterial effect in response to visible light.

By using the above-described method for producing a photocatalytic functional film, the photocatalytic functional film capable of maintaining a high-efficiency photocatalytic performance and solving the problem of decomposition of the substrate can be produced

BRIEF DESCRIPTION OF DRAWINGS

FIG. 1 is a schematic cross-sectional view of a photocatalytic functional film according to an exemplary embodiment of the present disclosure.

DETAILED DESCRIPTION

Hereinafter, exemplary embodiments of the present disclosure will be described in detail. However, exemplary embodiments are merely illustrative but not limiting. It is to be noted that the scope of the present disclosure is defined only by the claims.

Photocatalytic Functional Film

According to an exemplary embodiment of the present disclosure, a photocatalytic functional film has a structure of a substrate, a barrier layer and a photocatalytic layer stacked one on another. The barrier layer is a $SiO_2$ film, the photocatalyst layer comprises an amorphous $TiO_2$ film, and particles of visible light responsive photocatalytic material formed on the surface of the amorphous $TiO_2$ film.

Typically, in order to coat a visible light responsive photocatalyst material on the surface of an indoor interior material, a binder material for attaching the visible light responsive photocatalyst material, such as silica sol, is required.

However, in the process of coupling the binder material with the visible light responsive photocatalyst material, the binder material covers the surface of the visible light responsive photocatalyst material, such that the exposed area of the surface of the photocatalyst material is reduced. When this happens, there is a problem that the photocatalytic performance of the photocatalyst material is lowered, which realizes the surface reaction in the binder material.

In addition, if the photocatalyst material is directly coated on a substrate made of an organic material, the substrate may be decomposed by an organic material decomposition reaction of the photocatalyst material. When this happens, the stability of the substrate is lowered, and harmful substances may be generated due to decomposition of the substrate.

In view of the above, a $TiO_2$ amorphous sol has been developed as a binder material that can provide adhesive force without lowering the efficiency of the photocatalyst material.

The $TiO_2$ amorphous sol is a binder material which can prevent deterioration of the photoactivating ability of particles of the visible light responsive photocatalyst material during the process of forming a photocatalyst layer, thereby maintaining the photocatalytic performance obtained in the particle state as much as possible.

Further, in order to suppress decomposition of the substrate by the photocatalyst material, a barrier layer was provided between the substrate and the photocatalyst layer to prevent contact between the photocatalyst and the substrate.

The barrier layer is a $SiO_2$ film and may be formed by a $SiO_2$ sol, such that it has good adhesion with the substrate, good adhesion with the photocatalyst layer and high strength. Accordingly, the stability of the photocatalytic functional film can be improved.

FIG. 1 is a schematic cross-sectional view of a photocatalytic functional film according to an exemplary embodiment of the present disclosure. Referring to FIG. 1, the photocatalytic functional film 100 may include a structure of a substrate 10, a barrier layer 20, and a photocatalyst layer 30 stacked one on another.

The substrate 10 may be an indoor interior material. The interior material may include glass, wallpaper, tile film and the like. The photocatalyst layer 30 may be optically activated by the light introduced into a room to decompose the organic material, thereby achieving air purification, deodorization, antibacterial effect.

The barrier layer 20 may be a $SiO_2$ film. The barrier layer 20, which is the $SiO_2$ film, is provided between the substrate 10 and the photocatalyst layer 30. Accordingly, it is possible to prevent contact between the substrate and the photocatalyst layer, such that corrosion of the substrate caused by the photocatalyst of the photocatalyst layer can be prevented. In addition, the generation of harmful substances caused by the corrosion of the substrate can be suppressed, such that the stability of the substrate can be maintained over time For example, the $SiO_2$ film may be a porous film and may have a porosity of from approximately 5% to 50%, and a specific surface area of from approximately 5 $m^2/g$ to 500 $m^2/g$. Further, since the minimum strength is maintained, durability is given to the photocatalytic functional film layer, and the contact between the substrate and the photocatalyst layer can be reliably prevented.

The photocatalyst layer 30 may include an amorphous $TiO_2$ film; and particles of a visible light responsive photocatalytic material formed on the surface of the amorphous $TiO_2$ film. Since a binder material is necessary for attaching the particles of the visible light responsive photocatalyst material to the barrier layer 20, the $TiO_2$ film is formed by using the $TiO_2$ amorphous sol as the binder material. By doing so, adhesion between the photocatalytic layer and the barrier layer made of the $SiO_2$ film can be enhanced without lowering the luminous efficiency of the particles of the photocatalytic material.

The porosity of the amorphous $TiO_2$ film may range from approximately 5% to 50%. When the amorphous $TiO_2$ film has a porosity within the above range as a porous film, the catalytic activity efficiency of the particles of the visible light responsive photocatalyst with respect to visible light can be further improved.

On the other hand, if the amorphous $TiO_2$ film is densely formed with no porosity by a sputtering method or the like, adsorption of reactants such as formaldehyde is not efficiently carried out and thus photocatalytic activity may not be good.

The specific surface area of the amorphous $TiO_2$ film may range from approximately 5 $m^2/g$ to 500 $m^2/g$. When the amorphous $TiO_2$ film has a specific surface area within the above range, the catalytic activity efficiency of the particles of the visible light responsive photocatalyst material with respect to visible light may be better.

The amorphous $TiO_2$ film may be formed by a $TiO_2$ amorphous sol. The $TiO_2$ amorphous sol has good adhesion force and is advantageous to ensure transparency of the photocatalyst layer 30 formed by using the $TiO_2$ amorphous sol as a binder.

The $TiO_2$ amorphous sol is used in an amorphous state, as will be described below in the production method. Since the $TiO_2$ amorphous sol is used without crystallizing it, the $TiO_2$ particle size is smaller than that of crystallized one and thus it is possible to achieve transparency. The crystallized $TiO_2$ sol is already in a bonded state and thus has a small surface area and a low functional group content. On the other hand, the $TiO_2$ amorphous sol has a larger surface area and a higher functional group content, and thus has a good adhesion.

In addition, the $TiO_2$ amorphous sol may be prepared by using a sol-gel method in which dehydration and de-alcoholization are performed using an alcohol-based solvent, instead of water. A detailed description on a producing method will be given later.

Since the photocatalyst layer 30 includes particles of the visible light responsive photocatalytic material formed on the surface of the amorphous $TiO_2$ film, the particles of the visible light responsive photocatalytic material may be porous metal oxide particles carrying a visible light activating metal with porosity.

The porous metal oxide particles may include at least one selected from titanium oxide, tungsten oxide, zinc oxide, niobium oxide, and combinations thereof, and any material known as metal oxides may be used as long as it can be used as photocatalyst. The porous metal oxide particles have photoactivity mainly with respect to ultraviolet ray.

Any metal may be used as the visible light activating metal as long as it can give photoactivity with respect to visible light to the metal oxide. Specifically, the visible light activating metal may be, for example, a transition metal or a noble metal.

For example, the visible light activating metal may include at least one metal selected from the group consisting of tungsten, chromium, vanadium, molybdenum, copper, iron, cobalt, manganese, nickel, platinum, gold, cerium, cadmium, zinc, magnesium, calcium, strontium, and combinations thereof.

In addition, the visible light activating metal may be carried in the porous metal oxide particles in the form of an oxide of the above-described metals.

The particles of the visible light responsive photocatalyst material may be formed on the surface of the amorphous $TiO_2$ film by doping the visible light activating metal particles into pores in the porous metal oxide particles. The photocatalyst layer 30 thus formed may have optical activity with respect to visible light.

Since the particles of the visible light responsive photocatalyst include visible light activating metal particles having photoactivity with respect to visible light, they can have activity with respect to visible light as well as ultraviolet light and can absorb light over the entire visible light region. For example, the particles may have photoactivity with respect to visible light within the wavelength range of 380 nm to 780 nm.

The particles of the visible light responsive photocatalyst may achieve air purification, deodorization, antibacterial effect as electrons and holes generated from energy obtained by absorbing light generate superoxide anions or hydroxy radicals. For example, the superoxide anions or hydroxy radicals generated from the particles may decompose materials hazardous to the environment such as formaldehyde. Since the particles have a high absorption rate with respect to visible light and thus can exhibit a good efficiency even with an indoor light source, no additional ultraviolet ray supplier may be required.

The particles of the visible light responsive photocatalyst material may include a weight ratio of the porous metal oxide to the sum of the visible light activating metal and the visible light activating metal oxide in a weight ratio of approximately 99.9:0.1 to 99:1.

The thickness of the barrier layer may range from approximately 20 nm to 500 nm. The barrier layer prevents contact between the substrate and the photocatalyst layer. When the barrier layer has a thickness within the above range, it can prevent decomposition of the substrate layer by the photocatalyst. If the thickness of the barrier layer is less than approximately 20 nm, the amorphous $TiO_2$ film may not be formed sufficiently such that the substrate may not be sufficiently separated from the substrate. If the thickness of the barrier layer exceeds approximately 500 nm, it is not cost-efficient.

The thickness of the photocatalytic layer may range from approximately 50 nm to 500 nm. The photocatalyst layer contains the amorphous $TiO_2$ film and the particles of the visible light responsive photocatalyst, and the amorphous $TiO_2$ film is formed of the $TiO_2$ amorphous sol as a binder material. Accordingly, the adhesion to the barrier layer can be increased without lowering the photocatalytic efficiency of the particles, such that a stable photocatalytic functional film can be provided.

It is to be noted that the photocatalytic efficiency can be easily achieved when the thickness of the photocatalyst layer is within the above range. If the thickness of the photocatalyst layer is less than approximately 50 nm, the photocatalyst layer may not be formed properly, such that sufficient photocatalytic effect can not be achieved. If the thickness of the photocatalyst layer exceeds approximately 500 nm, some portions may not be involved in the photocatalytic reaction, and thus it is disadvantageous in terms of cost and efficiency.

Producing Method of Photocatalyst Functional Film

According to an exemplary embodiment of the present disclosure, a method for producing a photocatalytic functional film includes: adding an alcohol solvent and an acid to a silicate precursor to obtain a $SiO_2$ sol by dehydration and de-alcoholization reaction; applying and drying the $SiO_2$ sol on a substrate to form a barrier layer; adding an alcohol solvent and an acid to a titanium precursor to obtain a $TiO_2$ amorphous sol by dehydration and de-alcoholization reaction; and applying and drying a composition formed by mixing particles of visible light responsive photocatalyst material with the $TiO_2$ amorphous sol on the barrier layer, to form a photocatalyst layer.

The method for producing a photocatalytic functional film may include adding an alcohol solvent and an acid to a silicate precursor to obtain a $SiO_2$ sol by dehydration and de-alcoholization reaction.

The $SiO_2$ sol may be obtained by using a sol-gel method. Specifically, an alcohol solution is added to a silicate precursor, and an acid is used as a catalyst for dehydration and de-alcoholization by a hydrolysis reaction to obtain a $SiO_2$ sol.

Further, the method may include adding an alcohol solvent and an acid to a titanium precursor to obtain a $TiO_2$ amorphous sol by dehydration and de-alcoholization reaction.

The $TiO_2$ amorphous sol may be obtained by using a sol gel method. Specifically, an alcohol solution is added to a titanium precursor, and a $TiO_2$ amorphous sol can be obtained by dehydration and de-alcoholization by a hydrolysis reaction using an acid as a catalyst. Although no water is used in the sol-gel method, water may be added in the form of a solution mixed with an acid to be hydrolyzed. On the other hand, a hydrolysis reaction may occur, in which the alcohol group of the alkoxide precursor is substituted with the OH group by the acid.

The silicate precursor may be any known compound that can be used in a sol-gel method such as ethyl silicate. Specifically, tetraethyl orthosilicate, tetramethylorthosilicate, tetrabutylorthosilicate and the like may be used.

As the titanium precursor, any known compound may be used that can be used for a sol-gel method such as titanium alkoxide. Specifically, titanium tetraisopropoxide, titanium tetraethoxide, titanium tetrabutoxide and the like may be used.

The alcohol solvent may be at least one selected from the group consisting of isopropyl alcohol, ethanol, methanol, butanol, and combinations thereof.

The acid is used as a catalyst for dehydration and de-alcoholization reaction for the silicate precursor or the titanium precursor and the alcohol. Strong acids such as nitric acid and hydrochloric acid can be used as the acid.

The obtained $SiO_2$ sol is a solution in which nano-sized $SiO_2$ particles are dispersed in a colloidal state.

The obtained $TiO_2$ amorphous sol is a solution in which amorphous $TiO_2$ particles are dispersed in a colloidal state.

The obtained $SiO_2$ sol may be applied and dried on the substrate to form the barrier layer.

Further, a composition formed by mixing the particles of the visible light responsive photocatalyst material with the obtained $TiO_2$ amorphous sol may be applied and dried on the barrier layer to form the photocatalyst layer.

In addition, the composition for forming the photocatalyst layer may be prepared by mixing the particles of the visible light responsive photocatalyst material prepared separately with the obtained $TiO_2$ amorphous sol.

For example, the particles of the visible light responsive photocatalyst material may be prepared by preparing porous metal oxide particles, immersing it in a precursor solution of a visible light activating metal so that the visible light activating metal is infiltrated into the porous metal oxide particles in an ion state, and then reducing the ions of the visible light activating metal to a visible light activating metal to allow the ions to be supported within the porous metal oxide particles.

The particles of the visible light activating photocatalyst material have already been described above.

According to an exemplary embodiment of the present disclosure, the particles of the visible light activating photocatalyst material may be porous particles of $WO_3$ carrying Pt metal.

The composition may contain approximately 20 parts by weight of the $TiO_2$ amorphous sol relative to 100 parts by weight of the particles of the visible light responsive photocatalyst material. By using a $TiO_2$ amorphous sol within the above range, proper surface bonding for a large surface area can be obtained as the $TiO_2$ particles of the $TiO_2$ amorphous sol are small. On the other hand, if the content of the $TiO_2$ amorphous sol is too high, the surface of the particles of the visible light responsive photocatalyst material may be covered so that the reactivity may be lowered.

By using the above-described method for producing a photocatalytic functional film, the photocatalytic functional film capable of maintaining a high-efficiency photocatalytic performance and solving the problem of decomposition of the substrate can be produced.

Hereinafter, exemplary embodiments of the present disclosure will be described. It is to be understood, however, that the exemplary embodiments of the present disclosure described below are only for illustrative purposes and not intended to limit the present disclosure.

EXAMPLE AND COMPARATIVE EXAMPLES

Example 1

A 10 wt % solution of tetraethyl orthosilicate is prepared using ethyl alcohol as a solvent. After stirring for 30 minutes, a small amount of water and hydrochloric acid were added to hydrolyze it. Then, it was dehydrated and de-alcoholized by stirring for 1 hour to prepare a $SiO_2$ sol.

The film was applied on a PET film at the thickness of 100 nm and dried at room temperature to form a barrier layer.

On the other hand, a 10 wt % solution of titanium tetraisopropoxide is prepared by using isopropyl alcohol as a solvent. After stirring it for 30 minutes, a small amount of concentrated nitric acid was added and hydrolyzed. Subsequently, it was dehydrated and de-alcoholized by stirring for 30 minutes to form an amorphous $TiO_2$ sol.

Pt-supported $WO_3$ photocatalyst material particles were separately prepared.

50 parts by weight of the amorphous $TiO_2$ sol and 100 parts by weight of the Pt-supported $WO_3$ photocatalyst material were mixed to prepare a composition. The composition was applied on the barrier layer at the thickness of 100 nm by using a bar coater and dried at room temperature to form a photocatalyst layer, thereby producing a photocatalytic functional film.

Comparative Example 1

A photocatalytic functional film was produced in the same manner as in Example 1 except that a barrier layer was formed on a substrate.

Comparative Example 2

A 10 wt % solution of tetraethyl orthosilicate is prepared using ethyl alcohol as a solvent. After stirring for 30 minutes, a small amount of water and hydrochloric acid were added to hydrolyze it. Then, it was dehydrated and de-alcoholized by stirring for 1 hour to prepare a $SiO_2$ sol.

The $SiO_2$ sol was applied on the PET film at the thickness of 100 nm and dried at room temperature to form a barrier layer.

On the other hand, a 10 wt % aqueous solution of titanium tetraisopropoxide was prepared using distilled water as a solvent, and then it was stirred to produce a uniform precipitate. Then, a sufficient amount of nitric acid was added as an acid catalyst to obtain a transparent sol by condensation polymerization. It was stirred at 80° C. for more than 8 hours to prepare an opaque crystalline $TiO_2$ sol.

Pt-supported $WO_3$ photocatalyst material particles were separately prepared.

50 parts by weight of the crystalline $TiO_2$ sol and 100 parts by weight of the Pt-supported $WO_3$ photocatalyst material were mixed to prepare a composition, and the composition was applied on the barrier layer at the thickness of 100 nm using a bar coater and dried at room temperature to form a photocatalyst layer, thereby producing a photocatalytic function film.

Comparative Example 3

A 10 wt % solution of titanium tetraisopropoxide is prepared by using isopropyl alcohol as a solvent. After stirring for 30 minutes, a small amount of concentrated nitric acid was added and hydrolyzed. Then, it was dehydrated and de-alcoholized by stirring for 30 minutes to prepare amorphous $TiO_2$ sol.

A photocatalytic functional film was produced in the same manner as in Example 1 except that the amorphous $TiO_2$ sol was applied on the PET film at the thickness of 100 nm and dried at room temperature to form a barrier layer.

Experimental Example 1—Catalytic Properties of Photocatalytic Functional Films

The performance of removing formaldehyde of photocatalytic layers of Example 1 and Comparative Examples 1 and 2 was evaluated. The photocatalyst layers produced in Example 1 and Comparative Examples 1 and 2 were placed in a 20 L small chamber (manufactured by ADTEC Co.), and then clean air having a formaldehyde concentration of 0.08 ppm was continuously flown at the flow rate of 167 cc/min., such that ventilation was carried out 0.5 times/hr. A 10 W white fluorescent lamp was used as the light source, and the illuminance was set to be 1,000 lux. The formaldehyde removal rates were calculated by measuring the concentration before entering the chamber and the concentration after passing through the chamber, which is shown in Table 1 below. A 10 L of concentrated formaldehyde was prepared by using a DNPH (2,4-dinitrophenylhydrazine) cartridge and analyzed by a high performance liquid chromatography (HPLC from Agilent Technologies Inc.).

In addition, it was determined whether or not the PET films included in Example 1 and Comparative Examples 1 and 2 were damaged with naked eyes, results of which are shown in Table 1 below.

TABLE 1

| Photocatalytic Layer | Binder | Barrier Layer | Formaldehyde Removal Rate | Damage to PET Film |
|---|---|---|---|---|
| Example 1 | Amorphous TiO2 sol | Included | 80% | No damage |
| Comparative Example 1 | Amorphous TiO2 sol | Not included | 0% | Damage |
| Comparative Example 2 | Crystalline TiO2 sol | Included | 50% | No damage |

It can be seen from Table 1 that the particles of the visible light responsive photocatalyst material exhibit a luminous efficiency similar to that of the particle state even after forming the photocatalyst layer in Example 1. In contrast, in Comparative Examples 1 and 2, the luminous efficiencies are significantly lowered after the formation of the photocatalyst layer.

Specifically, in Comparative Example 1, it can be that the formaldehyde in the chamber could not be removed due to side reaction caused by the contact with the substrate layer.

On the other hand, it can be seen that the PET films according to Example 1 and Comparative Examples 2 each including an additional barrier layer between the substrate and the photocatalyst layer by the amorphous $TiO_2$ sol were not damaged. In contrast, the PET film according to Comparative Example 1 including no barrier layer was damaged.

Therefore, it can be seen that Example 1 includes a photocatalyst layer formed by using the amorphous $TiO_2$ sol as the binder material, such that good luminous efficiency can be achieved while damage to the PET film can be suppressed by virtue of the barrier layer.

Experimental Example 2—Physical Properties of Photocatalytic Functional Films

The pencil hardness of Example 1 and Comparative Examples 2 and 3 was measured with a pencil hardness tester (electric pencil hardness tester, Model 191, YUYU Instrument and Trade Co.) according to ASTM D3363.

TABLE 2

| Photocatalytic Layer | Binder | Barrier Layer | Type of Barrier Layer | Pencil Hardness |
|---|---|---|---|---|
| Example 1 | Amorphous TiO$_2$ sol | Included | SiO$_2$ Film | 2H |
| Comparative Example 2 | Crystalline TiO$_2$ sol | Included | SiO$_2$ Film | H |
| Comparative Example 3 | Amorphous TiO$_2$ sol | Included | Amorphous TiO$_2$ Film | B |

It can be seen that from Table 2 that the pencil hardness of Example 1 was superior to that of Comparative Examples 2 and 3.

Specifically, while both of Example 1 and Comparative Example 2 include the SiO$_2$ films as the barrier layers, Example 1 having the photocatalyst layer formed of the amorphous TiO$_2$ sol exhibited better pencil hardness over Comparative Example 2 having the photocatalyst layer formed of the crystalline TiO$_2$ sol.

In addition, while both of Example 1 and Comparative Example 3 include the photocatalyst layer formed of the amorphous TiO$_2$ sol, Example 1 having the barrier layer formed of the SiO$_2$ film exhibited better pencil hardness over Comparative Example 3 having the barrier layer formed of the TiO$_2$ film.

DESCRIPTION OF REFERENCE NUMERALS

100: Photocatalytic Functional Film
10: Substrate, 20: Barrier Layer, 30: Photocatalyst Layer

What is claimed is:

1. A photocatalytic functional film having a structure of a substrate, a barrier layer and a photocatalytic layer stacked one on another,
    wherein the barrier layer is a SiO$_2$ film, and
    wherein the photocatalyst layer is an amorphous TiO$_2$ film comprising particles of visible light responsive photocatalytic material,
    wherein the particles of the visible light responsive photocatalyst material are porous metal oxide particles carrying a visible light activating metal, and
    wherein the porous metal oxide particles comprise at least one selected from a group consisting of tungsten oxide, zinc oxide, and niobium oxide.

2. The photocatalytic functional film according to claim 1, wherein the amorphous TiO$_2$ film has a porosity of 5% to 50%.

3. The photocatalytic functional film according to claim 1, wherein the amorphous TiO$_2$ film has a specific surface area of 5 m$^2$/g to 500 m$^2$/g.

4. The photocatalytic functional film according to claim 1, wherein the amorphous TiO$_2$ film is a dried material of a TiO$_2$ amorphous sol.

5. The photocatalytic functional film according to claim 1, wherein the porous metal oxide particles carry the visible light activating metal as a visible light-activating metal or an oxide thereof, wherein the visible light activating metal comprises at least one of tungsten, chromium, vanadium, molybdenum, copper, iron, cobalt, manganese, nickel, platinum, gold, cerium, cadmium, zinc, magnesium, calcium, strontium, barium, or a combination thereof.

6. The photocatalytic functional film according to claim 1, wherein a weight ratio of the porous metal oxide and a sum of the visible light activating metal and a visible light activating metal oxide in the particles of the visible light responsive photocatalyst material ranges from 99.9:0.1 to 99:1.

7. The photocatalytic functional film according to claim 1, wherein a thickness of the barrier layer ranges from 20 nm to 500 nm.

8. The photocatalytic functional film according to claim 1, wherein a thickness of the photocatalytic layer ranges from 50 nm to 500 nm.

9. The photocatalytic functional film according to claim 1, wherein the substrate is an indoor interior material.

10. A method for producing a photocatalytic functional film, comprising:

adding an alcohol solvent and an acid to a silicate precursor to obtain a $SiO_2$ sol by dehydration and de-alcoholization reaction;

applying and drying the $SiO_2$ sol on a substrate to form a barrier layer;

adding an alcohol solvent and an acid to a titanium precursor to obtain a $TiO_2$ amorphous sol by dehydration and de-alcoholization reaction; and applying and drying a composition formed by mixing particles of visible light responsive photocatalyst material with the $TiO_2$ amorphous sol on the barrier layer, to form a photocatalyst layer, wherein the photocatalytic layer is an amorphous $TiO_2$ film comprising particles of visible light responsive photocatalytic material, wherein the particles of the visible light responsive photocatalyst material are porous metal oxide particles carrying a visible light activating metal, and wherein the porous metal oxide particles comprise at least one selected from a group consisting of tungsten oxide, zinc oxide, niobium oxide, and a combination thereof.

11. The method according to claim 10, wherein the alcohol solvent is at least one selected from a group consisting of isopropyl alcohol, ethanol, methanol, butanol, and a combination thereof.

12. The method according to claim 10, wherein the composition comprises 20 parts by weight of the $TiO_2$ amorphous sol with respect to 100 parts by weight of the particles of the visible light responsive photocatalyst material.

* * * * *